(12) United States Patent
Browning et al.

(10) Patent No.: US 7,008,224 B1
(45) Date of Patent: Mar. 7, 2006

(54) DISPOSABLE DENTAL INSTRUMENT

(75) Inventors: Jerry W. Browning, 42035 Liberty Dr., Hemet, CA (US) 92544; David G. Murphy, 438 Walden Dr., Otsego, MI (US) 49078; Thomas P. Crooks, 606 Larkspur Ave., Corona Del Mar, CA (US) 92625; Brian Babson, Fountain Valley, CA (US)

(73) Assignees: Jerry W. Browning, Hemet, CA (US); David G. Murphy, Ostego, MI (US); Thomas P. Crooks, Corona del Mar, CA (US)

( * ) Notice: Subject to any disclaimer, the term of this patent is extended or adjusted under 35 U.S.C. 154(b) by 0 days.

(21) Appl. No.: 10/800,144

(22) Filed: Mar. 12, 2004

Related U.S. Application Data

(60) Provisional application No. 60/455,078, filed on Mar. 13, 2003.

(51) Int. Cl.
*A61C 1/02* (2006.01)
*A61C 1/05* (2006.01)

(52) U.S. Cl. ..................... 433/104; 433/132
(58) Field of Classification Search ................ 433/104, 433/114, 117, 126, 131, 132; 403/270, 285; 264/442, 443, 445
See application file for complete search history.

(56) References Cited

U.S. PATENT DOCUMENTS 5,263,606 A * 11/1993 Dutt et al. ................... 220/613
5,308,242 A * 5/1994 McLaughlin et al. ........ 433/114
5,348,473 A * 9/1994 Kivlighan, Jr. ............. 433/114
5,352,118 A * 10/1994 Franetzki et al. ............. 433/82
5,538,425 A * 7/1996 Reeves et al. ................ 433/82
5,681,409 A * 10/1997 Lin et al. .................... 156/73.1
5,772,436 A * 6/1998 Matsui et al. ............... 433/126
6,186,784 B1 * 2/2001 Bailey ........................ 433/126
6,305,935 B1 * 10/2001 Cardarelli ................... 433/126

* cited by examiner

*Primary Examiner*—Todd E. Manahan
(74) *Attorney, Agent, or Firm*—Knobbe, Martens, Olson & Bear, LLP

(57) ABSTRACT

A disposable dental instrument of the compressed air drive type is disclosed for use in performing dental procedures on a workpiece. The disposable dental instrument is constructed from two mating shells and a core. Each shell incorporates a mating surface and the shells are joined using various bonding methods to ensure a waterproof, high quality dental instrument. An elongated body has conduits penetrating a base at one end of the body. The conduits allow entry of a light beam, a pressurized water stream, and a compressed air stream into the body. The base includes attachment threads for securing the body to a source of the light beam, pressurized water stream, and compressed air stream. Pluralities of passageways are in communication with the conduits for conducting the light beam, the water stream, and the air stream through the body. A head at the opposite end of the body rotatably mounts a turbine shaft on bearing surfaces which inhibit vibration and noise. The turbine shaft includes a turbine impeller and a clamping hole for removable attachment of a dental bur to the shaft. The air stream drives the impeller at a high speed for rotating the bur about a rotational axis. An opening in the body adjacent to the head allows release of the light beam, the pressurized water stream, and a portion of the compressed air stream in a direction toward the distal end of the bur so that the bur, the light beam, the water stream, and the air stream may all converge on the workpiece.

47 Claims, 10 Drawing Sheets

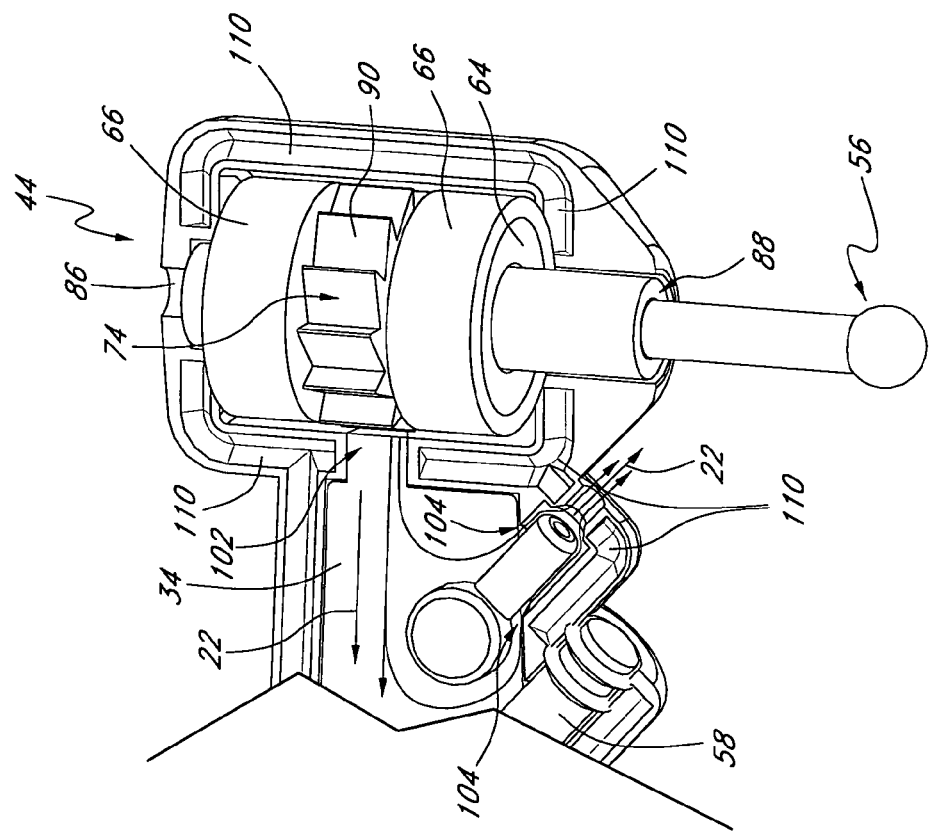
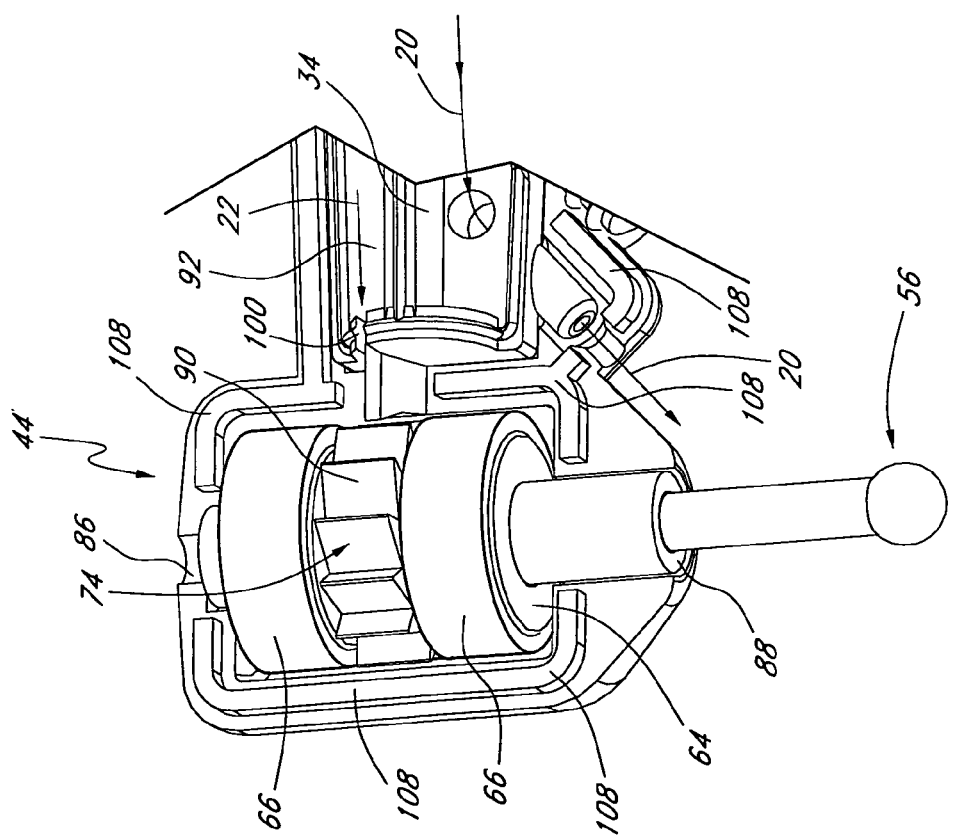

DISPOSABLE DENTAL INSTRUMENT

This application claims the benefit of U.S. Provisional Application No. 60/455,078 filed Mar. 13, 2003 entitled "DISPOSABLE DENTAL INSTRUMENT," the entire contents of which is expressly incorporated by reference.

FIELD OF THE INVENTION

The present invention relates generally to a hand held instrument for dental procedures, and more particularly to an improved disposable hand held instrument for dental drilling procedures.

BACKGROUND OF THE INVENTION

Many dental procedures necessitate the use of specialized instruments such as, but not limited to, various dental hand tools and syringes. It is well known that infectious agents such as viruses and bacteria can be transmitted from one person to another through re-use of incompletely sterilized medical instruments, such as dental drills.

SUMMARY OF THE INVENTION

The present invention is a disposable dental instrument of the compressed air drive type for use in performing dental procedures on a workpiece, such as a tooth or filling. In one embodiment, an elongated body has conduits penetrating a base at one end of the body. The conduits allow entry of a light beam, a pressurized water stream, and a compressed air stream into the body. The base includes attachments for securing the body to a source of the light beam, pressurized water stream, and compressed air stream. Pluralities of passageways are in communication with the conduits for conducting the light beam, the water stream, and the air stream through the body. The body includes an outer shell and a core. The outer shell can be constructed as a hollow one piece shell or a pair of mating shells. The mating shells are joined to define a cavity within, and can be easily formed with conventional injection molding techniques. The cavity wall comprises a first set of integrally formed groves, and the core provides a second set of integrally formed groves for mating with the first set of grooves. When mated, the first set and the second set of integrally formed grooves are matched in shape such that the enclosed passageways are thereby formed along the longitudinal axis of the body.

In one embodiment, a head at the end of the elongated body retains bushings which provide a bearing support for a high speed turbine impeller shaft. The rotatable shaft includes a turbine impeller and a removable attachment device for attachment of a dental bur to the shaft. The air stream drives the impeller at a high rotational velocity for rotating the bur about a rotational axis.

In another embodiment, the head contains bushings which support separate bearings rotatably mounting the impeller shaft. The shaft includes a turbine impeller and a removable attachment means for attachment of a dental bur to the shaft. The air stream drives the impeller at a high speed for rotating the bur about a rotational axis.

An opening in the body adjacent to the head allows release of the light beam, the pressurized water stream, and a portion of the compressed air stream in a direction toward the distal end of the bur so that the bur, the light beam, the water stream, and the air stream all converge on the workpiece to enable illumination, cooling, and removal of debris from the workpiece during the dental procedures. Preferably, one passageway contains a transparent, light-conducting rod for conducting the light beam efficiently from the base to the opening. A major portion of the air stream is directed to the turbine impeller, and a minor portion of the air stream is diverted to move through one of the passageways, through the opening, and toward the workpiece.

The preferred embodiments of this invention are inexpensive to manufacture, thereby making it practical to dispose of after use with one patient. Such use considerably reduces the risk of spreading disease between patients. The preferred embodiments are lightweight, easy to grasp and manipulate, and quickly connects to a standard source of air, water, and light and facilitate quick and easy replacement of various sizes and shapes of dental burs, making it unnecessary to use more than one disposable drill with each patient. Another feature of the preferred embodiment allows the quick exchange of dental burs without significantly increasing the size of the device. Another feature of the preferred embodiment enable delivering water, air and light to the work site in a single dental instrument. The preferred embodiments additionally provide a high degree of torque and control to the dental bur, making it easy and comfortable for the dental practitioner to use. Another advantage of the preferred embodiments is that they can be mass produced using advanced plastic welding practices to provide a completely sealed housing eliminating possible air and water leaks and include an improved bearing housing and production procedure to ensure smooth, quiet bearing operation and increased durability and additionally provide a high degree of torque and control to the dental bur, making it easy for the dental practitioner to use.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

These and other features, aspects and advantages of the present invention will now be described with reference to the drawings of a preferred embodiment, which is intended to illustrate and not to limit the invention. The drawings comprise four figures.

FIG. 8 is a detailed cross sectional right side view illustrating the impeller assembly.

FIG. 9 is a detailed cross sectional left side view illustrating the impeller assembly;

DETAILED DESCRIPTION OF THE PREFERRED EMBODIMENT

Figure 1:
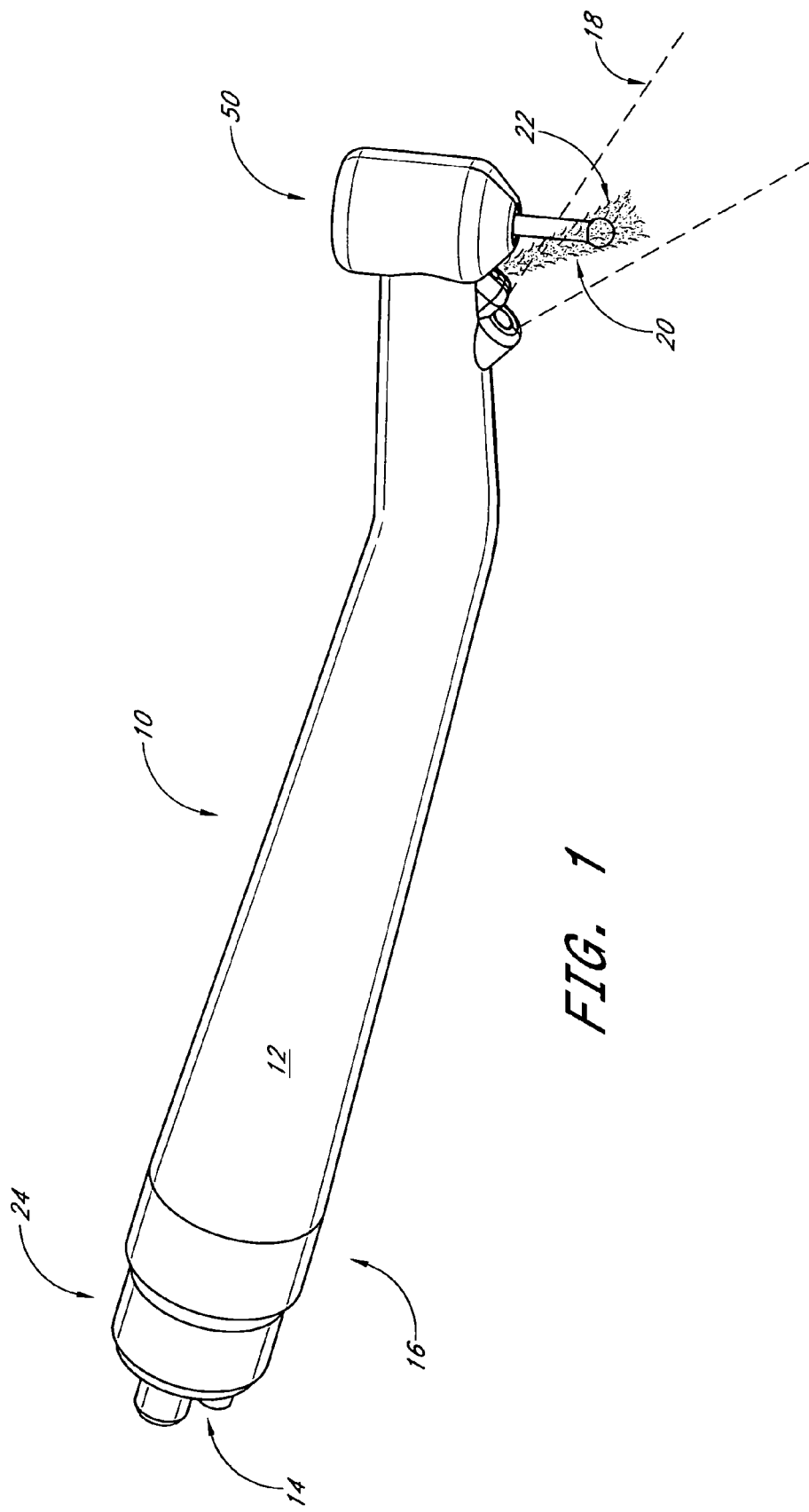
FIG. 1 is a side perspective view of a dental instrument in accordance with a preferred embodiment of the present invention.

With reference to FIG. 1 an overall view of a disposable dental instrument of the compressed air drive type is shown. The disposable dental instrument is used in performing dental procedures on a workpiece, such as a tooth or filling. A portable, elongated body 10 has an exterior surface 12, which can have a variety of different textures or coatings suited for allowing firm grasping and manipulation of the body 10. Conduits 14 penetrate a base 16 of the body 10 at one end of the body 10 and allow entry of a light beam 18, a pressurized water stream 20, and a compressed air stream 22 into the body 10. Conduits 14 further provide an exit from the body 10 of a return air stream. The base 16 further includes an attachment system 24 for securing the body 10 to a source (not shown) of the light beam 18, pressurized water stream 20, and compressed air stream 22. Preferably the attachment system 24 can be an external thread formed integrally on the base 16, for mating with an internal thread on the source (not shown). A gasket (not shown) between the end of the base 16 and the source will prevent leakage of air and water past this internal thread of the source and the external thread of the base. A plurality of internal passageways 26 (shown in FIG. 2) are in communication with the conduits 14 for conducting the light beam 18, the water stream 20, and the air stream 22 through the body 10. In one embodiment of the invention, water is introduced into the air stream for providing lubrication to the turbine shaft and additional power for driving the turbine described below. Preferably, the present invention can be made entirely or partially of a relatively inexpensive material, such as plastic, whereby the invention is inexpensive enough to be disposed of after use, or given to a patient perhaps to be used at a later date.

Figure 2:
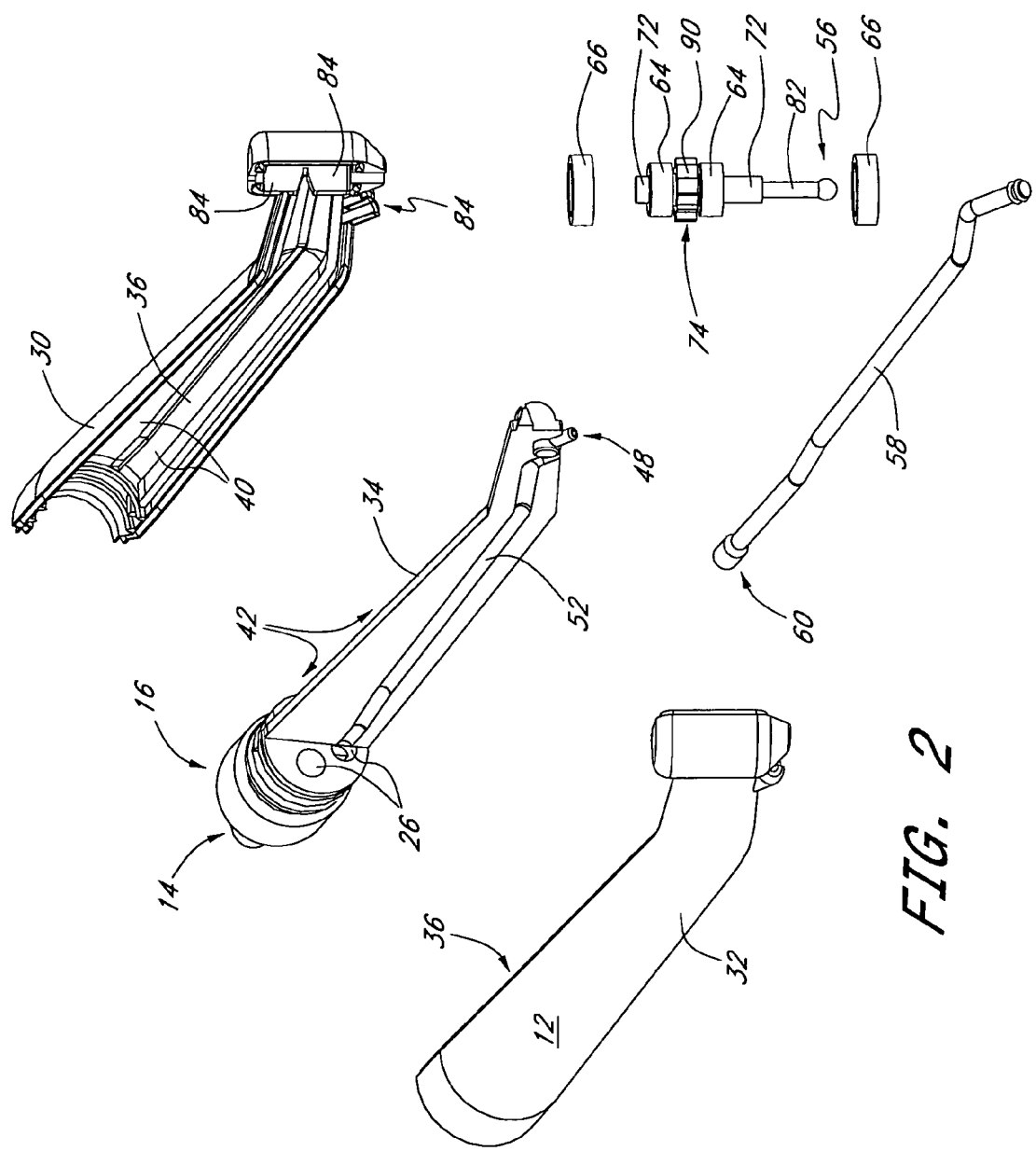
FIG. 2 is an exploded view of the dental instrument illustrating all components.

As seen in the embodiment of FIG. 2, the body 10 can be constructed from a left shell half 30, a right shell half 32, and a core 34. The left and right shell halves 30, 32 are joined to establish the exterior surface 12 of the body 10 and to define a cavity 36 within, and can be easily formed with conventional injection molding techniques. The cavity 36 comprises a first set 40 of integrally formed groves aligned generally with the longitudinal axis of the body 10. The core 34 provides a second set 42 of integrally formed groves for mating with the first set 40 of grooves. When mated, the first set of grooves 40 and the second set 42 of integrally formed grooves are matched in shape such that the enclosed passageways 26 are thereby formed primarily along the longitudinal axis of the body 10.

Figure 3:
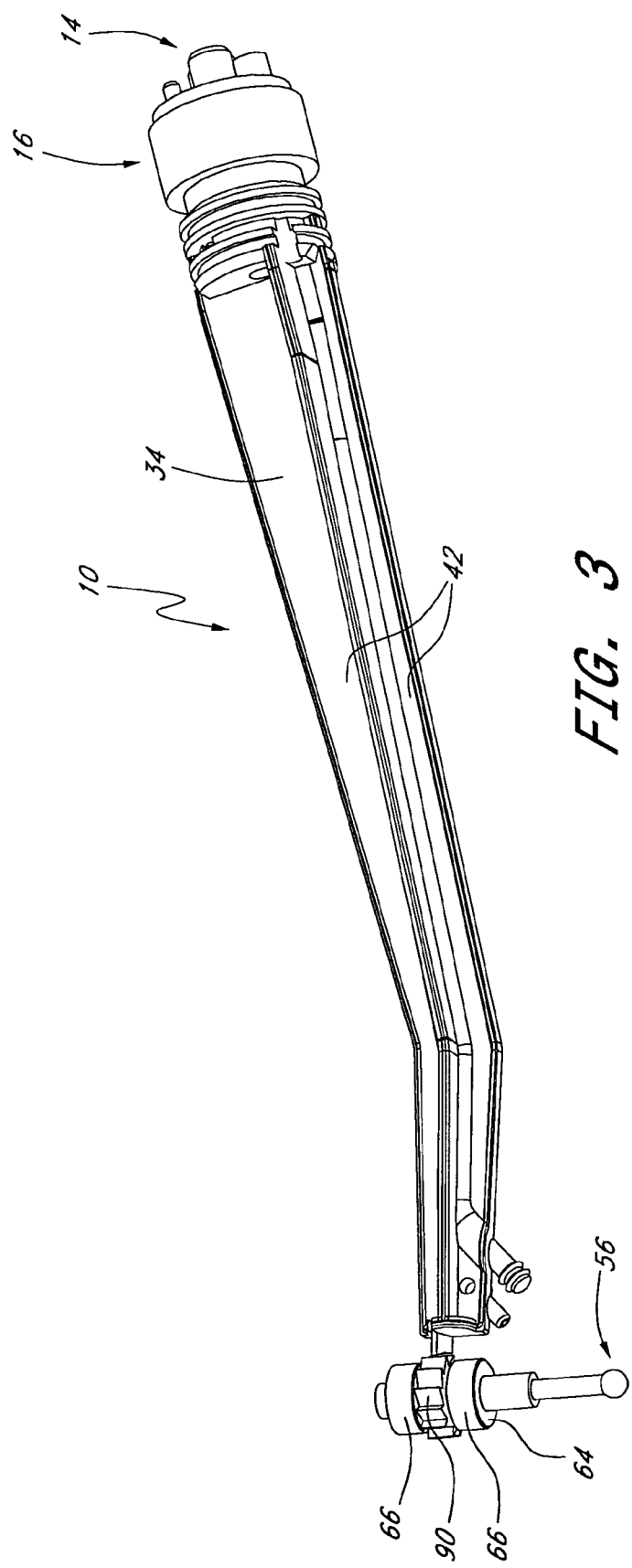
FIG. 3 is a partial left side cross-sectional view of the dental instrument illustrating air passageways, a light rod, and an impeller assembly.

FIG. 3 shows a detailed perspective view of the left side of the core 34 without the shell halves 30 and 32. In one embodiment of the present invention the integrally formed grooves 42 allow compressed air and water to enter through the base 16 and travel laterally along the core 34 towards a head 44.

Figure 4:
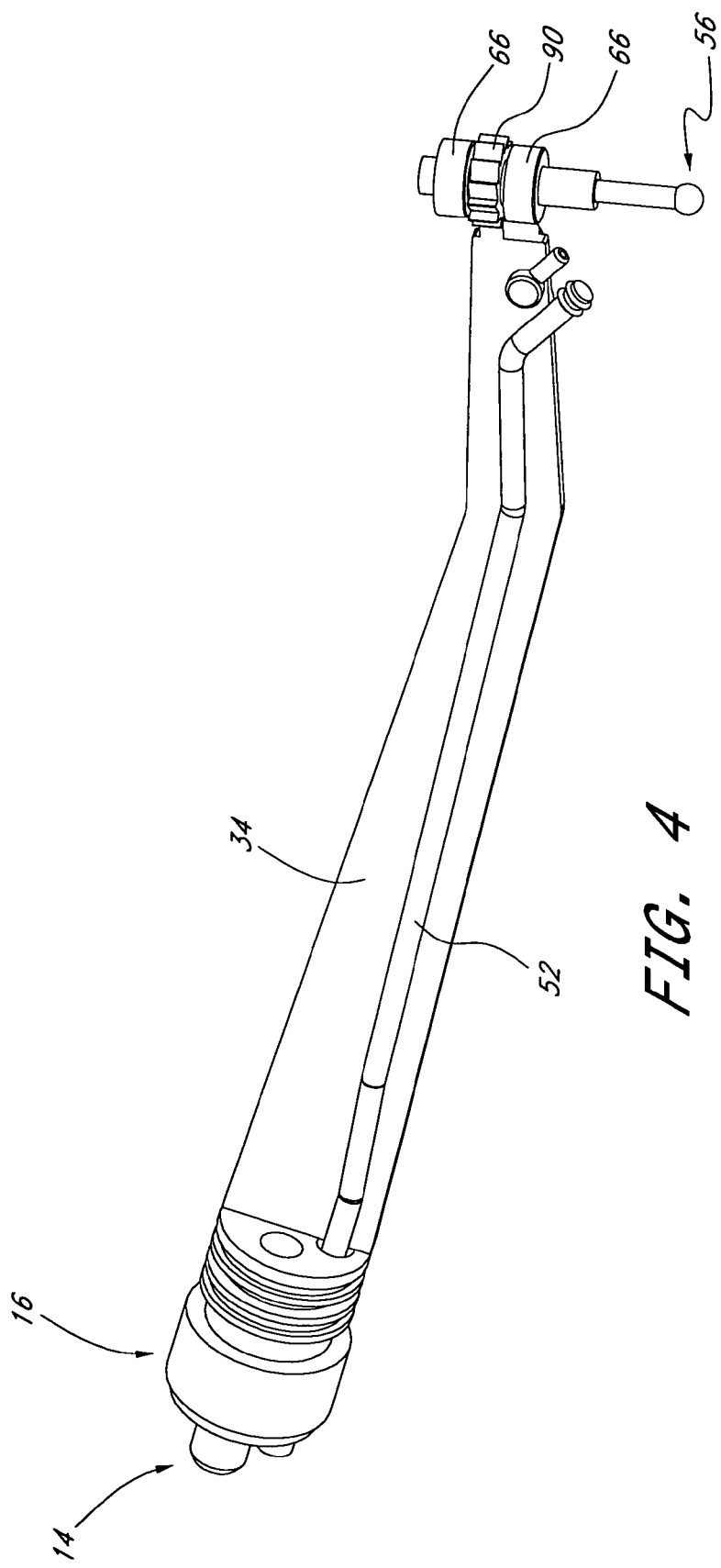
FIG. 4 is a partial right side view of the dental instrument illustrating a center core, the light rod and the impeller assembly.

FIG. 4 shows a detailed perspective view of the right side of the core 34 without the shell halves 30 and 32. Returning air from the head 44 travels laterally along the right side of the core 34 to return to the base 16. A light tube 52 can be positioned within the right side of the core 34 to allow light to travel from the base towards the head 44.

In another preferred embodiment of the invention, the body 10 can be constructed from a one-piece hollow outer shell (not shown) and the core 34. Similarly to the left and right shell halves 30, 32, the one-piece hollow shell comprises the exterior surface 12 of the body 10 and defines the cavity 36 within. The core 34 is advantageously positioned in the cavity 36 within the one-piece outer shell. The one-piece outer shell can also be easily formed with conventional injection molding techniques. All internal cavities within the body 10 matching the core 34 are identically constructed in both the two-piece outer shell embodiment as well as the one-piece outer shell embodiment.

Figure 5:
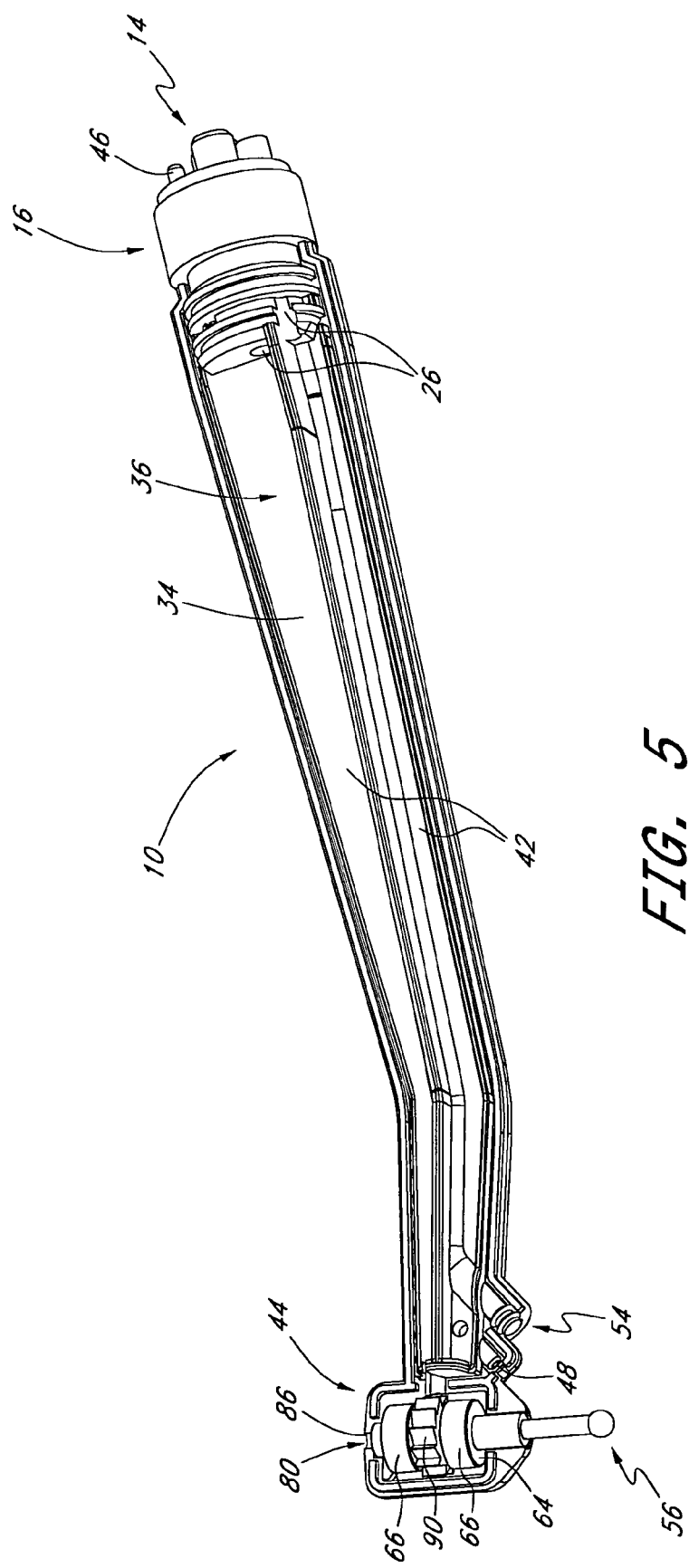
FIG. 5 is a cross-sectional right side view of the dental instrument illustrating air and water passageways, and the impeller assembly.

FIGS. 5 and 8 illustrate one embodiment of the invention where in one of the conduits 14, designated as a tubular conduit 46 for carrying the water stream 20 is positioned to penetrate the base 16. The water stream 20 is directed from the conduit 46 laterally around the core 34 to reach a position generally lateral to the core. Thereafter, the water moves longitudinally adjacent to the under surface of the core 34 to reach a water stream opening or nozzle 48 for ejection of the water stream 20.

Figure 6:
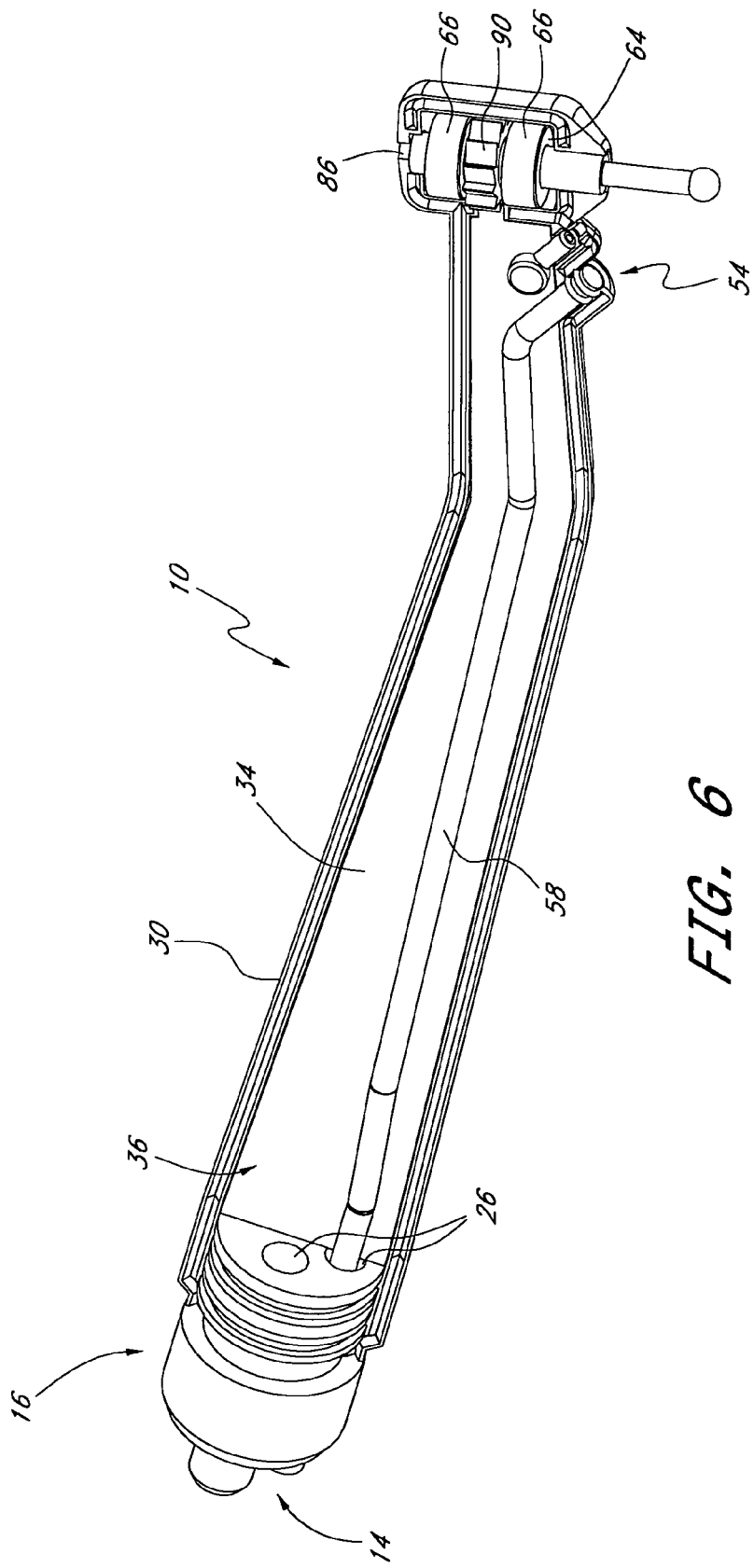
FIG. 6 is a cross-sectional right side view of the dental instrument illustrating internal components.

A light opening 54 in the body 10 adjacent to the head 44 allows release of the light beam 18. A portion of the compressed air steam 22 or a portion of the returning compressed air can surround the stream water opening 48 where the pressurized water stream 20 along with the portion of compressed air flow in a direction toward the distal end of a dental bur 56. The dental bur 56, the light beam 18, the water stream 20, and the air stream 22 all converge on the workpiece to enable illumination, cooling and removal of debris from the workpiece during the dental procedure. A light-conducting rod 58 (FIG. 6) fills the light opening 54. Other light transmitting systems such as, but not limited to fiber optics are also possible. Preferably, one of the passageways 26 contains the transparent, light conducting rod 58 having a highly polished surface for conducting the light beam 18 efficiently from the base 16 to the light opening 54. Likewise, one of the tubular conduits 14 preferably contains a highly polished light conducting rod stub 60 for efficiently conducting the light beam 18 through the base 16 from the source of the light (not shown) to the light conducting rod 58.

The head 44 at the other end of the body 10 contains bearings 64 that are positioned in bushings 66 attached to an upper portion 68 and a lower portion 70 of a supporting shaft 72. The bushings 66 can simplify the bearing installation, decrease noise and vibration, and provide a cushioning effect allowing the dentist to receive a feedback feeling while working. The bushings 66 can be made from a variety of different materials including, but not limited to, rubber, plastic, metal, or a composite. The bearings 64 can be attached to the bushings 66 by a press fit, a specific fastener, glue, or an epoxy. The bushings 66 allow for accurate positioning of the bearing 64 within the head 44 inhibiting disturbing vibration and noise that can occur while performing a procedure on a workpiece. A reduction of vibration and noise allows for a more comfortable environment for the patient during a dental procedure.

Figure 7:
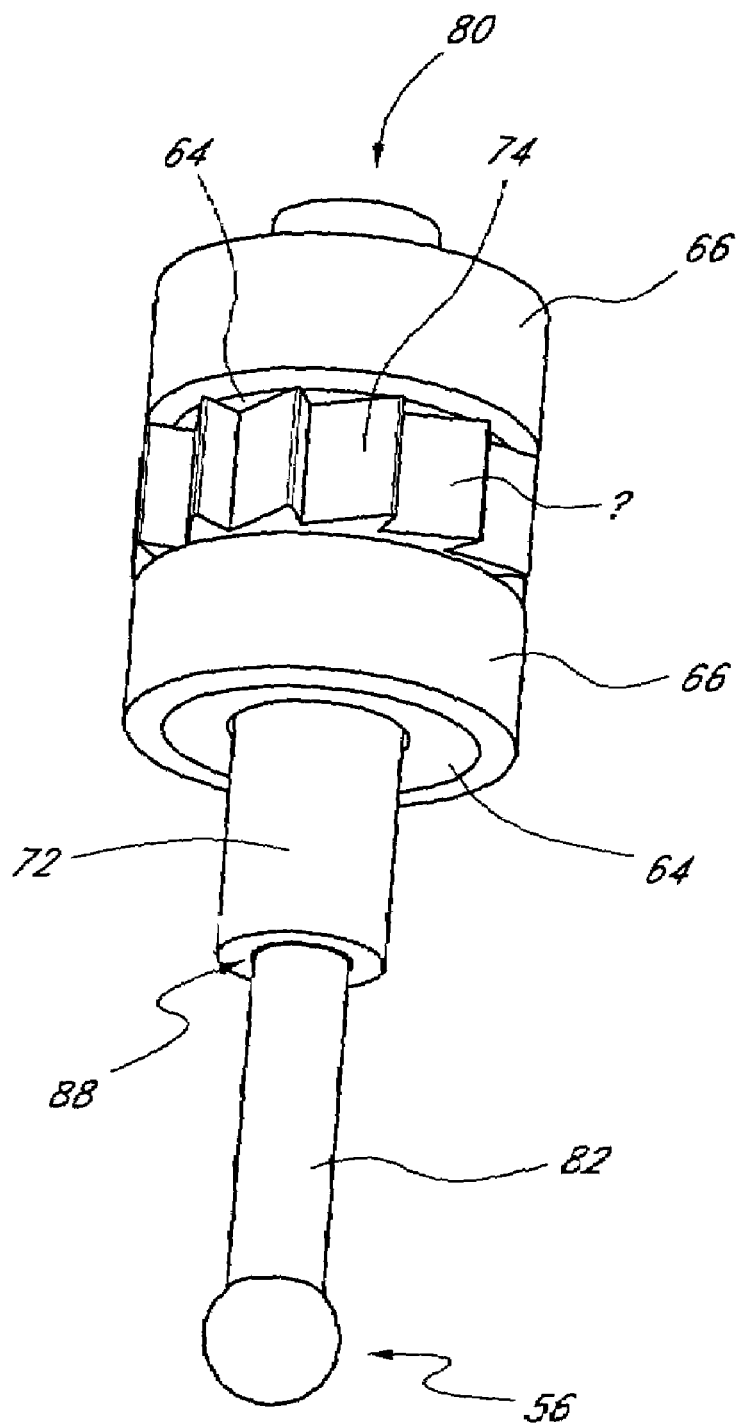
FIG. 7 is a detailed perspective view illustrating the impeller assembly, bearings, and drill bur.

As illustrated in FIG. 7, the supporting shaft 72 includes a turbine impeller 74 and a bur removal system, preferably a through hole 80 for inserting a removal tool to poke a dental bur 56 out of the supporting shaft 72. Other dental bur removal systems such as a dental bur ejector, where a built in mechanism is incorporated in the disposable dental instrument to assist in the removal of the dental bur are also possible. The air stream 22 drives the impeller 74 at a high speed for rotating the bur 56 about a rotational axis. The dental bur 56 is supported by a clamping system (not shown) in a downwardly projecting direction from the head 44. The dental bur 56 includes a bur mounting shaft 82, and can be any of a number of different dental tools for example, but not limited to a drill bit, a prophylactic cup, a polisher, or a diamond cutting tool.

The head 44 further includes a pair of mounting cavities 84 (FIG. 2) for accepting the bushings 66. The bearing 64 are advantageously positioned within the bushings 66. The mounting cavities 84 are formed so as to urge the bushings 66 and as a result the outer races of the bearings 64 toward each other to achieve a predetermined amount of preload. As such, the support shaft 72 is confined to rotational motion only, with lateral motion of the support shaft 72 being significantly limited.

As the disposable dental tool of the present invention does not require long-term functional reliability, the bearings 64 can be conventional, metallic bearings, or, alternatively, may be formed from less expensive, non-metallic materials such as hard plastic. In one preferred embodiment of the present invention, the bearings 64 can be designed as floating bearings where the bearings are completely surrounded by a floating medium such as water, air, oil, or any combination thereof. The floating medium can be supplied to the floating bearings under pressure or the bearings can be enclosed in a chamber filled the floating medium to ensure minimal friction decreasing vibration and noise.

Figure 10:
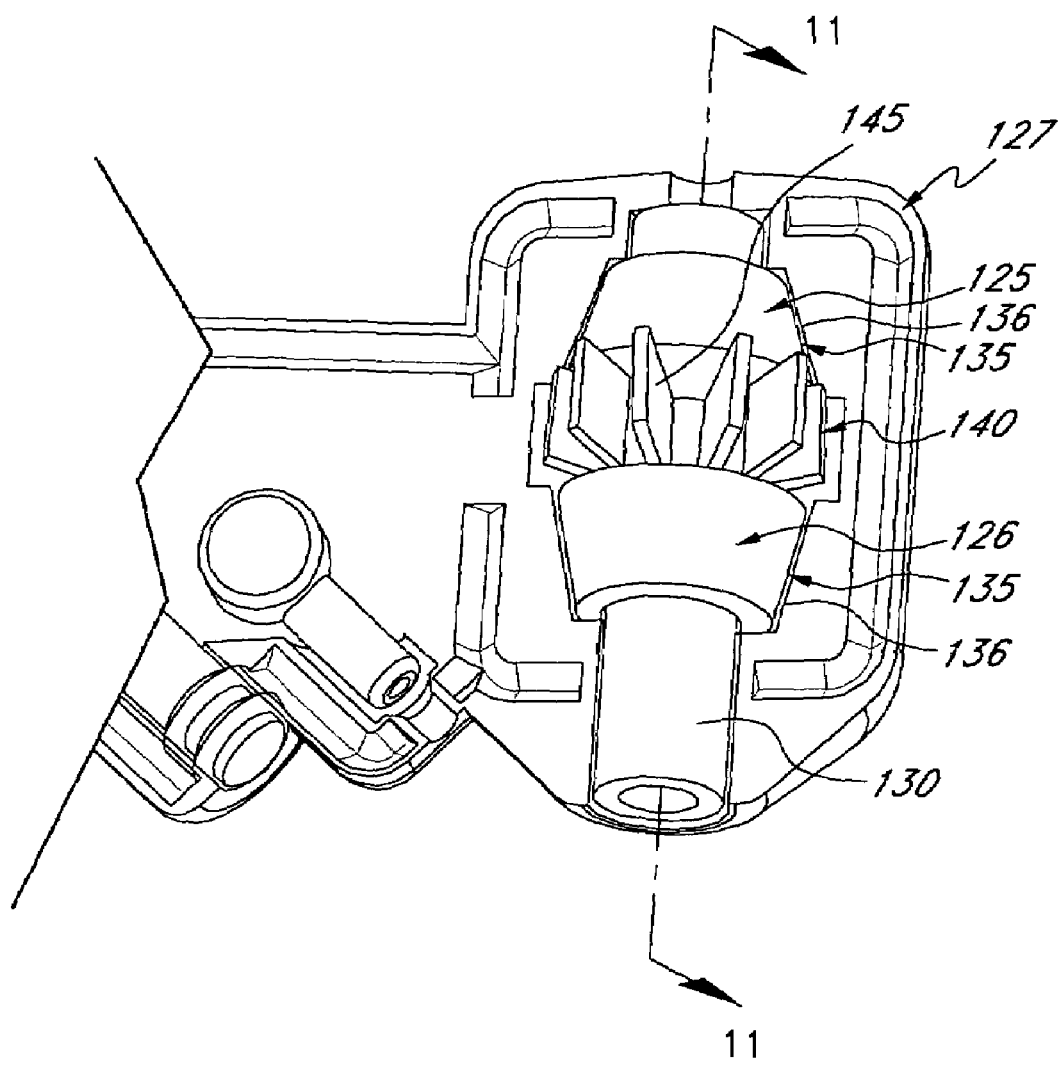
FIG. 10 illustrates another embodiment of the impeller assembly having a paddle-wheel vane configuration.
Figure 11:
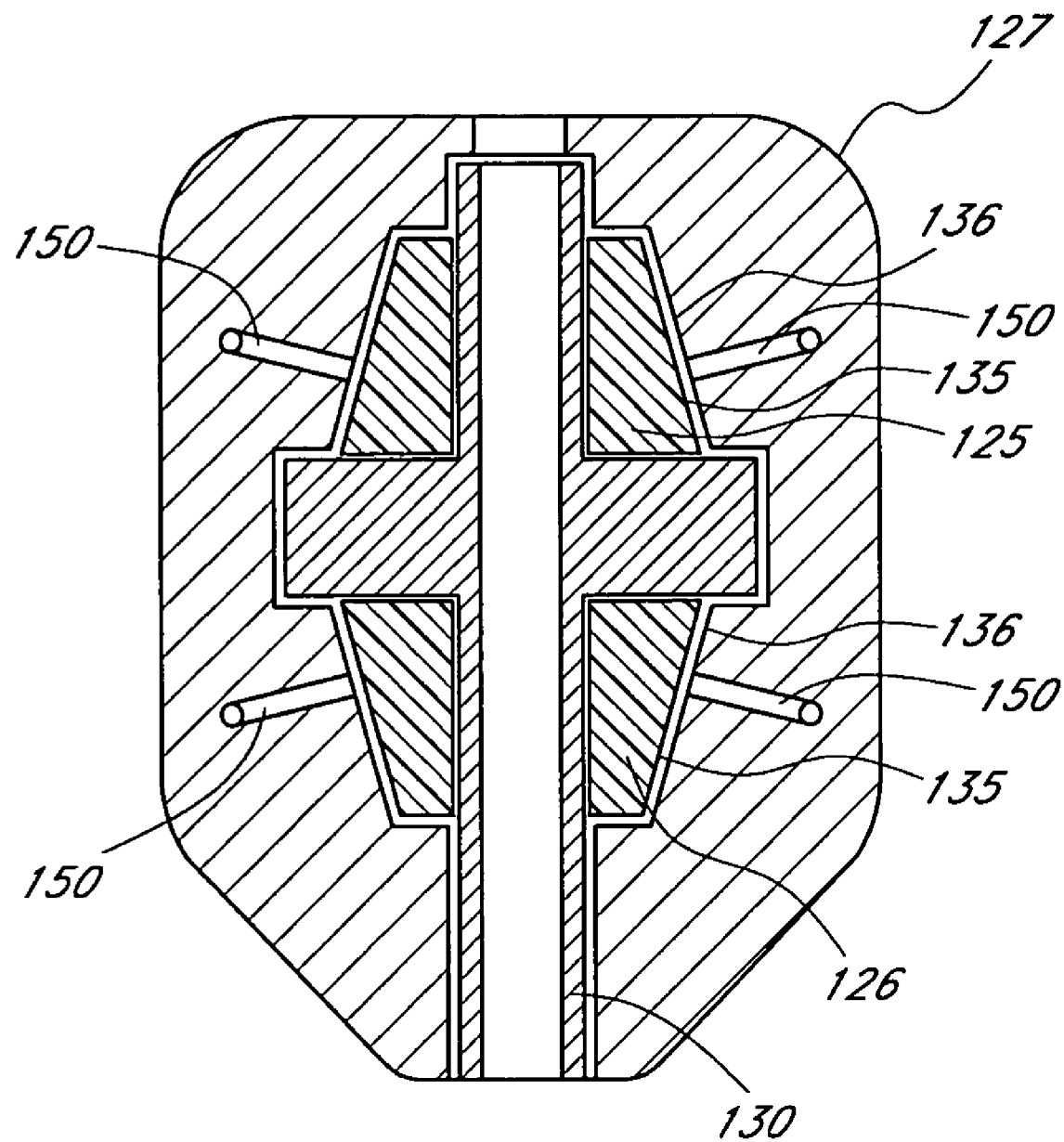
FIG. 11 is a detailed cross-sectional view of the impeller assembly of FIG. 10 in which the impeller shaft rotates on internal bearing surfaces of cone shaped bushings supported within the body of the dental instrument.

Another preferred embodiment of the invention is shown in FIGS. 10 and 11 in which bushings 125 and 126 are mounted within the head 127 of the dental instrument. The impeller shaft 130 is rotatably supported by these bushings and the interior wall of the bushings provide the bearing surface for the impeller shaft to rotate at a high velocity. Bushings 125 and 126 may be constructed from a suitable metal including scintered metal or a suitable plastic such as Teflon.

Advantageously, the bushings 125, 126 have a cone-shaped external configuration 135 in engagement with a corresponding cone-shaped cavity 136 within head 127 to limit lateral movement of the shaft 130 relative to the bushings 125, 126.

Conduits 150 in the cone shaped cavity can be used to introduce water or other lubricant under pressure to the interior bearing wall surfaces of the bushings which support the impeller shaft 130 when the impeller shaft 130 is caused to rotate to thereby further reduce friction between the shaft 130 and bearing surfaces of the bushings 125, 126. In one embodiment, the water under pressure is forced through the walls of bushings 125, 126 formed of a porous materal such as sintered metal to lubricate this internal bearing surface. The use of a lubricant also enables quieter operation of the drill for the benefit of both the dental practitioner and the patient.

In one preferred embodiment of the invention shown in FIGS. 7–9, the bur clamping system of the support shaft 72 includes a clamping hole 88 that is aligned with the rotational axis of the support shaft 72. The clamping hole can have a smaller diameter than that of the bur mounting shaft 82, whereby the clamping hole can provides an interference fit to the bur mounting shaft 82. The clamping hole can have a series of relief cutouts (not shown) to permit a sidewall (not shown) to be forced open to accommodate the bur mounting shaft 82. The bur 56 can be inserted into the clamping hole to be held tightly in place by the sidewall. The head 44 further includes an access hole 86 aligned approximately with the rotational axis of the support shaft 72 and the bur removal system, whereby the dental bur 56 may be disengaged from the support shaft 72 so as to insert a new dental bur. The support shaft 72 provides for self-center and allows repeated disengagement and insertion of the dental bur 56.

FIGS. 8 and 9 illustrate detailed views of one embodiment of the dental instrument head 44, the air, water, and light distribution area, and the mating surfaces used to ensure a strong, precise connection free of air and water leaks. The mating surfaces will be described in greater detail below.

A major portion of the air stream 22 is directed to the turbine impeller 74. The impeller 74 has a plurality of blades 90 for receiving the stream of air 22. The air stream 22 can be directed against the impeller blades 90 through at least one separate air passage 92. The air passage can comprise a variety of different shaped nozzles 100 allowing for efficient transfer of compressed air energy against the blades 90 to provide rotational torque to drive the impeller 74. One or more of the nozzles 100 can be positioned relative to the impeller 74 so that at least one of the blades 90 receives a portion of the air stream 22 primarily orthogonally to the surface of at least one of the blades 90 at each rotational position of the impeller 74. This precise injection of air onto the surface of the impeller blades 90 can provide a consistent high rotational torque force on the dental tool.

The air nozzle 100 for directing the air stream 22 against the blades 90 of the impeller 74 can be designed using different shapes. A second embodiment of the present invention can incorporate a venturi to accelerate the air stream to provide a faster air stream. A faster air stream can allow for an improvement turbine driving efficiency.

Various different shapes of turbine blades can be used to efficiently turn the impeller 74 and provide more efficient torque as well as quieter operation providing a comfortable environment for the dental instrument user and patient. For example, a cup shaped turbine blade can be used to more efficiently translate the compressed air energy into a strong rotational torque. Another embodiment of the impeller blade is shown in FIG. 10, wherein the impeller 140 has paddle-wheel configured blades 145 to provide improved rotational torque.

In operation, a dental practitioner selects an approximate dental bur 56 for the required dental procedure and inserts the bur mounting shaft 82 of the dental bur 56 into the clamping hole of the support shaft 72. The sidewall (not shown) of clamping hole 88 flexes to allow insertion of the bur mounting shaft, at least some of the sidewall material is displaced into relief cutouts (not shown). The dental practitioner then uses the attachment system 24 of the body 10 to connect the base 16 of the body 10 to a source of pressurized water, pressurized air, and light. During a typical dental procedure, the dental practitioner activates the pressurized air and light together at the source, and activates the pressurized water with a foot pedal or other actuator for cooling the workpiece and flushing away debris.

When he activates the pressurized water source, such as through a foot pedal or other control means on the source (not shown), water is forced through one of the conduits 14 of the base 16 at a position above the core 34. The water then travels laterally around the core 34 to reach a position lateral to the core 34, and then through one groove or passageway 42 toward the head 44. The stream of water then exits through the water stream opening 48 in a direction toward the distal end of the dental bur 56, so as to flush away debris and apply water to the workpiece for cooling. The water stream opening 48 can be adjustable to allow more or less water to flow from the disposable dental instrument.

When the light source is activated, light travels through the light conducting rod stub 60 through the base 16 to the light conducting rod 58, where it is passed through the opening 54 toward the workpiece, thereby illuminating the workpiece. Fiber optics can also be used in place of the light-conducting rod 58. The focus of light exiting the opening 54 can be adjustable to provide the operator with a well-illuminated work area.

When the pressurized air source is activated, the air stream 22 flows through one of the conduits 14, through one of the grooves or passageways 42, and passes through the air nozzle 100 for directing the air stream 22 against the blades 90 of the impeller 74. The force of the air against the blades 90 causes the impeller 74 to rotate, thereby driving the dental bur 56. The air then leaves the head 50 through at least one return air passage 102. A minor portion of the returning air stream 22 can be diverted to move through an aperture 104 surrounding the water nozzle 48. This minor portion of the air stream 22 can be directed along with the water stream 20 toward the workpiece to remove debris from the workpiece. The returning air can also blow away debris from the workpiece without water to dry the workpiece.

Once the dental procedure requiring the bur 56 has been completed, the dental practitioner then pokes an elongated object through the access hole 86 of the head 44 to remove the dental bur 56 from the clamping hole 88. A new bur may be inserted, or, if all procedures are complete, the disposable hand tool of the present invention may be discarded.

To ensure high quality, completely aligned, leak free mating of the two shell halves 30 and 32, specific mating surfaces are incorporated into each shell half. FIG. 8 illustrates a protruding square angled mating surface 108 that is positioned along the outer edge of the right shell half 32 and advantageously surrounds the end of the light rod 58 and the apertures 98. FIG. 9 illustrates a triangular shaped recess surface 110 along the outer edge of the left shell half 30 that advantageously surrounds the end of the light rod 58 and the apertures 104. The triangular shaped recess surface 110 is positioned directly opposite from the square angled mating surface 108 of the right shell half 32.

The shell halves 30, 32 can be joined together using a variety of different production procedures including, but not limited to, heated plastic welding, sonic plastic welding etc. As the two shell halves 30 and 32 are positioned together during production, the angular surface of the triangular shaped recess 110 of the shell half 30 allows the square angled mating surface 108 of shell half 32 to advantageously align itself with the triangular shaped recess surface 110. During the joining procedure the extra material of the square angled mating surface provides sufficient material to allow for a complete joining of the two shell halves 30 and 32. The sufficient material and accurate alignment joining design provide a strong, a leak-free disposable dental instrument that operates efficiently.

Of course, the foregoing description is that of a preferred construction having certain features, aspects, and advantages in accordance with the present invention. Various changes and modifications may be made to the above-described arrangements without departing from the spirit and scope of the invention, as defined by the appended Embodiments.

What is claimed is:

1. A disposable dental instrument driven by compressed air comprising:
   an elongated body, said elongated body comprising:
   a first shell, a second mating shell, and a core, said first and second shells joined to form an exterior surface for manual manipulation, said shells forming a cavity, said cavity comprising a first set of integrally formed grooves within a cavity wall, said core comprising a second set of integrally formed grooves matching up with said first set of grooves, said first and second set of grooves being matched in shape and location to define various passageways as fluid conduits;
   a base, said base comprising:
   a plurality of conduits, said base communicating with an outside source of light, air, and water through said conduits, said conduits communicating with said passageways defined by said elongated body;
   a head located at the opposite end from said base, said head comprising:
   a supporting shaft, bearings rotatably supporting an upper and lower end of said supporting shaft, each bearing positioned within a bushing, said bushings positioned within said head, a turbine impeller, said turbine impeller connected to said supporting shaft, said turbine impeller being driven by said compressed source air through an air nozzle to rotate a dental bur, a dental bur mounting system, a dental bur removal system, said dental bur removal system having an access hole to allow an object to push out said dental bur from said supporting shaft, at least one of said plurality of conduits extending from said base to said bearings and configured to guide water from said outside source to said bearings; and
   various openings located proximate to said head, said various openings delivering light, air, and water in the general direction of said dental bur.

2. A disposable dental instrument driven by compressed air comprising:
   an elongated body, said elongated body comprising:
   a first shell, a mating second shell, and a core, said first and second shells joined to form an exterior surface for manual manipulation, said shells forming a cavity, said cavity comprising a first set of integrally formed grooves within a cavity wall, said core comprising a second set of integrally formed grooves matching up with said first set of grooves, said first and second set of grooves being substantially matched in shape and location to define various passageways as fluid conduits;
   a base, said base comprising:
   a plurality of conduits, said base communicating with an outside source of light, air, and water through said conduits, said conduits communicating with said passageways defined by said elongated body;
   a head located at the opposite end from said base, said head comprising:
   a rotatable turbine shaft, first and second bushings mounted within said head and rotatably supporting said turbine shaft, a turbine impeller located between said first and second bushings and attached to said rotatable turbine shaft;
   said turbine impeller being juxtaposed an air nozzle connected to said compressed air source by one of said fluid conduits so as to drive the impeller with the air; and
   a dental bur mounting apparatus attached at one end of said turbine shaft, at least one of said conduits extending from said base to the turbine shaft and configured to direct water from the outside source to the turbine shaft.

3. The disposable dental instrument of claim 2, wherein said elongated body is angled.

4. The disposable dental instrument of claim 2, wherein said elongated body is made substantially entirely of plastic.

5. The disposable dental instrument of claim 2, wherein said elongated body is made partially of plastic.

6. The disposable dental instrument of claim 2, wherein said elongated body is made partially of metal.

7. The disposable dental instrument of claim 2, wherein exterior surfaces of said shell halves are coated with rubber.

8. The disposable dental instrument of claim 2 having a fiber optic conduit communicating with an outside source of light.

9. The disposable dental instrument of claim 2, wherein said turbine impeller incorporates straight turbine blades.

10. The disposable dental instrument of claim 2, wherein said turbine impeller incorporates curved turbine blades.

11. The disposable dental instrument of claim 2, wherein said turbine impeller has a paddlewheel configuration.

12. The disposable dental instrument of claim 2, wherein said air nozzle incorporates a venturi.

13. The disposable dental instrument of claim 2 having an opening for delivering light in the general direction of said dental bur.

14. The disposable dental instrument of claim 13 said light is configured to have adjustable focus.

15. The disposable dental instrument of claim 2 having an opening delivering water in the general direction of said dental bur.

16. The disposable dental instrument of claim 15 where said opening for delivering water is configured to be adjustable.

17. The disposable dental instrument of claim 2, wherein said shaft includes bearings mounted within said bushings supported by said head.

18. The disposable dental instrument of claim 17, wherein said bearings are made of plastic.

19. The disposable dental instrument of claim 17, wherein said bearings are made of metal.

20. The disposable dental instrument of claim 17, wherein said bearings are sealed.

21. The disposable dental instrument of claim 17, wherein said bearings are lubricated under pressure.

22. The disposable dental instrument of claim 21, wherein said lubricant is oil.

23. The disposable dental instrument of claim 21, wherein said lubricant is water.

24. The disposable dental instrument of claim 21, wherein said bearings are floating within a lubricant.

25. The disposable dental instrument of claim 21, wherein said lubricant is oil.

26. The disposable dental instrument of claim 21, wherein said lubricant is water.

27. The disposable dental instrument of claim 21, wherein said bushings are made of rubber.

28. The disposable dental instrument of claim 2, wherein said shaft is rotatably mounted by bushings supported by said head and said bushings provide internal bearing surfaces for said shaft.

29. The disposable dental instrument of claim 28, wherein said bushings are made of plastic.

30. The disposable dental instrument of claim 28, wherein said bushings are made of metal.

31. The disposable dental instrument of claim 28, wherein said brushings are made of sintered metal.

32. The disposable dental instrument of claim 31, wherein one of said conduits conducts water under pressure to said bushing so that said water is forced through the walls of said bushings to lubricate the internal bearing surfaces thereof.

33. The disposable dental instrument of claim 28, wherein said bushings have an outer cone shaped configuration adapted to engage a cone-shaped wall within said head to limit lateral movement of said shaft within said head.

34. A disposable dental instrument driven by compressed air comprising:

an elongated body, said elongated body comprising:
a first shell half, a second shell half, and a core, said shell halves joined to form an exterior surface for manual manipulation, said halves forming a cavity, said cavity comprising a first set of integrally formed grooves within a cavity wall, said core comprising a second set of integrally formed grooves matching up with said first set of grooves, said first and second set of grooves being matched in shape and location to define various passageways as fluid conduits;

a base, said base comprising:
a plurality of conduits, said base communicating with an outside source of light, air, and water through said conduits, said conduits communicating with said passageways defined by said elongated body;

a head located at the opposite end from said base, said head comprising:
a supporting shaft rotatably mounted within said head, a turbine impeller, said turbine impeller connected to said supporting shaft, said turbine impeller being driven by said outside source of air through an air nozzle to rotate a dental bur, a dental bur mounting system, a dental bur removal system, said dental bur removal system having an access hole to allow an object to push out said dental bur from said supporting shaft;

various openings located under said head, said various openings delivering light, air, and water in the general direction of said dental bur; and a shell half joining system incorporating said first shell half and said second shell half, said first shell half incorporating a square angled protruding surface along the entire joining edge of said first shell half, said square angled protruding surface defining a first width, said second shell half incorporating a triangular shaped recess surface along the entire joining edge of said second shell half, said triangular shaped recess including first and second slated walls extending from said joining edge inwardly and toward each other, said slanted walls at the joining edge defining a second width that is larger than the first width, and defining a third width that is smaller than the first width at a central portion of the triangular shaped recess, said square angled protruding surface designed to integrally join with said triangular shaped recess surface to form a strong, water and air proof connection.

35. The disposable dental instrument of claim 34, wherein said elongated body is angled.

36. The disposable dental instrument of claim 34, wherein said elongated body is made entirely of plastic.

37. The disposable dental instrument of claim 34, wherein said elongated body is made partially of plastic.

38. The disposable dental instrument of claim 34, wherein said elongated body is made partially of metal.

39. The disposable dental instrument of claim 34, wherein said exterior surface is coated with rubber.

40. The disposable dental instrument of claim 34, wherein at least one of said conduits communicating with said outside source of light is made of fiber optics.

41. The disposable dental instrument of claim 34, wherein said turbine impeller incorporates straight turbine blades.

42. The disposable dental instrument of claim 34, wherein said turbine impeller incorporates curved turbine blades.

43. The disposable dental instrument of claim 34, wherein said air nozzle incorporates a venturi.

44. The disposable dental instrument of claim 34, wherein one of said openings delivering light is configured to provide adjustable focus of said light.

45. The disposable dental instrument of claim 34, wherein one of said openings delivering water is configured to be adjustable.

46. The disposable dental instrument of claim 34, wherein said shell half-joining system incorporates plastic heat welding.

47. The disposable dental instrument of claim 34, wherein said shell half-joining system incorporates various frequencies of sonic frequency welding.

* * * * *

UNITED STATES PATENT AND TRADEMARK OFFICE
CERTIFICATE OF CORRECTION

| | |
|---|---|
| PATENT NO. | : 7,008,224 B1 |
| APPLICATION NO. | : 10/800144 |
| DATED | : March 7, 2006 |
| INVENTOR(S) | : Browning et al. |

Page 1 of 1

It is certified that error appears in the above-identified patent and that said Letters Patent is hereby corrected as shown below:

At column 5, line 51, please delete "materal" and insert --material--, therefore.

At column 7, line 64, please delete "Embodiments." and insert --embodiments.--, therefore.

Signed and Sealed this

Seventeenth Day of October, 2006

JON W. DUDAS
*Director of the United States Patent and Trademark Office*